(12) United States Patent
Fiedler et al.

(10) Patent No.: US 7,778,787 B2
(45) Date of Patent: Aug. 17, 2010

(54) TIMING CALIBRATION FOR TOF-PET SCANNER

(75) Inventors: Klaus Fiedler, Aachen (DE); Michael Geagan, Wayne, PA (US); Gerd Muehllehner, Wayne, PA (US); Walter Ruetten, Linnich (DE); Andreas Thon, Aachen (DE)

(73) Assignee: Koninklijke Philips Electronics N.V., Eindhoven (NL)

(*) Notice: Subject to any disclaimer, the term of this patent is extended or adjusted under 35 U.S.C. 154(b) by 574 days.

(21) Appl. No.: 11/573,557

(22) PCT Filed: Aug. 2, 2005

(86) PCT No.: PCT/IB2005/052587
§ 371 (c)(1),
(2), (4) Date: Feb. 12, 2007

(87) PCT Pub. No.: WO2006/018766
PCT Pub. Date: Feb. 23, 2006

(65) Prior Publication Data
US 2007/0270693 A1    Nov. 22, 2007

Related U.S. Application Data

(60) Provisional application No. 60/601,210, filed on Aug. 13, 2004.

(51) Int. Cl.
*A61B 6/00* (2006.01)

(52) U.S. Cl. .............................. 702/85; 702/38; 702/39; 702/40; 702/79; 702/89; 702/104; 702/106; 702/107; 702/125; 702/176; 702/178; 378/207; 250/363.09; 600/436

(58) Field of Classification Search ............. 702/38–40, 702/79, 85, 89–20, 104, 106–107, 125, 176–178; 378/207; 250/363.09; 600/436
See application file for complete search history.

(56) References Cited

U.S. PATENT DOCUMENTS

| | | | |
|---|---|---|---|
| 4,543,478 A | 9/1985 | Nunley et al. | |
| 5,986,266 A | 11/1999 | Andreaco et al. | |
| 6,072,177 A | 6/2000 | McCroskey et al. | |
| 6,327,546 B1 * | 12/2001 | Petrillo et al. | 702/89 |
| 6,452,164 B1 | 9/2002 | Andarawis et al. | |
| 2003/0021375 A1 * | 1/2003 | Jones et al. | 378/51 |

FOREIGN PATENT DOCUMENTS

| | | |
|---|---|---|
| GB | 1528360 | 10/1978 |
| JP | 61132888 A | 6/1986 |
| SU | 1122114 | 5/1988 |
| WO | 9949494 A1 | 9/1999 |

* cited by examiner

*Primary Examiner*—Sujoy K Kundu

(57) ABSTRACT

A time-of-flight PET nuclear imaging device (A) includes radiation detectors (20, 22, 24), electronic circuits (26, 28, 30, 32) for processing output signals from each of detectors (20), a coincidence detector (34), a time-of-flight calculator (38) and image processing circuitry (40). A calibration system (48) includes an energy source (50, 150) which generates an electrical or optical calibration pulse. The electrical calibration pulse is applied at an input to the electronics at an output of the detector and the optical calibration pulse is applied to a preselected point adjacent a face of each optical sensor (20) of the detectors. A calibration processor (52) measures the time differences between the generation of the calibration pulse and the receipt of a trigger signal from the electronic circuitry by the coincidence detector (34) and adjusts adjustable delay circuits (44, 46) to minimize these time differences.

17 Claims, 4 Drawing Sheets

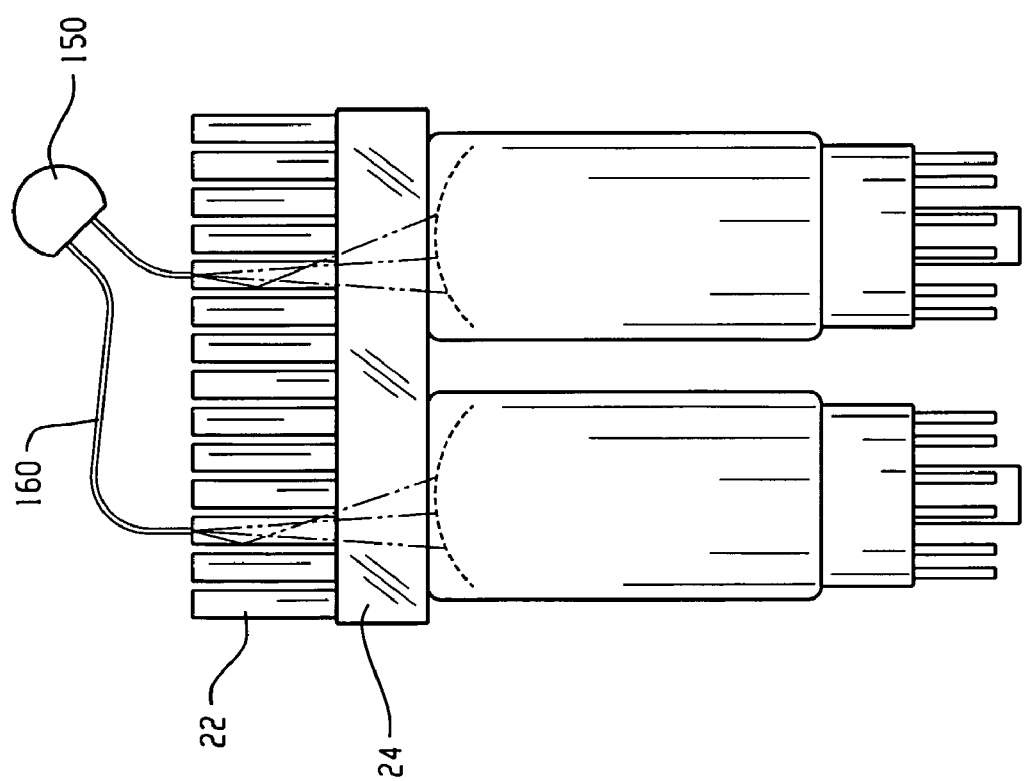

TIMING CALIBRATION FOR TOF-PET SCANNER

CROSS REFERENCE TO RELATED APPLICATIONS

This application claims the benefit of U.S. provisional application Ser. No. 60/601,210 filed Aug. 13, 2004, which is incorporated herein by reference.

The present application relates to the digital imaging arts. It finds particular application in connection with the calibration of a time-of-flight-positron emission tomography (TOF-PET), positron emission tomography (PET), coincidence-capable gamma camera medical imaging systems, and the like, and will be described with particular reference thereto. It is to be appreciated that it may also find application in other types of nuclear cameras as well as other types of diagnostic imaging where temporal calibrations are performed.

Nuclear medicine imaging involves the detection of radiation, such as gamma photons, from a subject under investigation. Gamma cameras, also known as nuclear medicine cameras, are used in medical and other devices to detect the intensity and the spatial position of radioactive energy. In medical devices, the gamma camera detects radioactive energy from radioactive materials that have been placed by medical personnel in, for example, the blood stream of a patient for performing medical tests and imaging of various vital organs.

A gamma camera typically includes one or more detector heads each having an array of scintillation crystals that is positioned above an array of photo-multipliers. When a gamma photon interacts with a scintillation crystal, a cascade of lower energy photons, typically in the visible or UV band, is emitted, termed an "event." The nearest light detectors, typically photomultiplier tubes (PMTs), in turn, detect the cascade of lower energy photons and each produces an electrical signal in the form of a pulse. Electronics interpret the signals to provide a video display and/or image of the spatial position and energy of the radiation source in the subject.

Positron Emission Tomography (PET) imaging differs from a conventional gamma ray imaging in that the isotopes injected emit positrons as they decay. When the positron collides with an electron (an annihilation event) two gamma photons are emitted simultaneously in opposite directions. Gamma cameras used for PET imaging typically include laterally spaced rings of detectors which encircle the patient. The analog signals from the detectors, typically scintillators and PMTs, on opposite sides of the ring are analyzed by coincidence detection circuits to detect the coincident or simultaneous receipt of gamma photons which are indicative of annihilation events. If two events are detected coincidentally, a line of response (LOR) is defined between the two detector points. These LORs are reconstructed into the diagnostic image. Gamma photons which reach the respective detectors outside a preselected coincidence window are assumed to be the result of unrelated random events and are ignored. In some studies, coincident events can be only 1% of all detected radiation. It is desirable to have the window relatively narrow to reduce the number of "randoms" that are detected in the coincidence window. The erroneous signals that result from random simultaneous detection of two different radiation events create false LORs and degrade the final image.

Time-of-flight (TOF)-PET scanning involves the determination of not only the LOR, but also the location along the LOR at which the annihilation event occurred. With gamma radiation tracking 30 cm/ns, and detector diameters being on the order of 90-150 cm, very precise detection time measurements are needed to determine time-of-flight information.

For various reasons, the reporting time between radiation impact and the signals indicating detection of events arriving at the coincidence detector varies between PMTs and detector heads. Physical variations in the PMTs and scintillation crystal as well as variance in the length of cables used to carry signals associated with different PMTs, circuit components, circuit temperature, and the like contribute to these variations. A significant source of variation in the reporting time is in the electronic hardware between the PMT and the coincidence circuit. If the coincident signal from one PMT is received by the coincidence detector significantly earlier or later than from another PMT, inaccuracies tend to result. These inaccuracies may include false detection indications of coincidence, incorrect time-of-flight determinations, and images with compromised quality. In a PET scanner, if the collision of one photon of an annihilation pair with one detector is not reported within the coincidence window of being simultaneous, the coincident event is missed.

The gamma camera is calibrated to ensure the reporting of events is accurate. The calibration typically adjusts the spatial gain and offset of the array of photo-multipliers to insure spatial and energy accuracy. The timing of each light detection channel can be calibrated relative to all other channels to compensate for temporal differences between signals triggered by the same event but received at different PMTs and detector heads, for example by incorporating timing delays or in the coincidence determination software. Some of the timing differences tend to be stable over a relatively long period. Differences due to cable lengths or position of individual scintillator pixels relative to the PMTs tend to be of this type. Timing differences may also change within a shorter time, for example, those caused by temperature dependence of the electronics, changes in gain and threshold settings, and the like. These changing timing errors again reduce image quality.

Conventionally, the calibration has been performed with one or more radioactive point sources. The emitted quanta are converted into optical photons by the scintillator pixels. However, the achievable time resolution is limited by the photon statistics of this conversion process. To obtain a sufficient accuracy for all channels, a long measurement time and/or a strong source are employed. This renders frequent calibrations generally impractical. As a result, drift due to temperature effects and other short term variations are not readily corrected.

Recently, calibration techniques which rely on the pulsing of a light source have been developed. The light source is coupled to the detector. Trigger signals from various zones of the detector are simultaneously examined by a calibration circuit and information collected by the calibration circuit is used to calibrate delays of trigger signals of the detector with respect to each other.

The present invention provides a new and improved method and apparatus which overcome the above-referenced problems and others.

In accordance with one aspect of the present invention, a calibration system is provided for a PET nuclear imaging device which includes radiation detectors, electronic circuitry for processing output signals from the detectors, a coincidence detector, and image processing circuitry. The calibration system includes an energy source which provides an energy output to generate calibration pulses. A means is provided for communicating the calibration pulses to each of the radiation detectors or electronic circuits to generate trigger pulses indicative of times the calibration pulses are received.

A calibration processor determines differences in time of the receipt of the trigger pulses from each of the electronic circuits by the coincidence detector. The calibration processor adjusts programmable delays in each of the electronic circuits to reduce the determined time differences.

In accordance with another aspect of the present invention, a method is provided for calibrating a nuclear imaging system that includes radiation detectors, electronic circuits for processing output signals from the detectors, a coincidence detector, and image processing circuitry. The method includes activating an energy source to generate a calibration pulse. The calibration pulse is communicated to each of the detectors or electronic circuits to cause the electronic circuits to generate trigger pulses, the trigger pulses traveling to the coincidence detector. Differences in time between the generation of the calibration pulse and receipt of the corresponding trigger pulse from each of the electronic circuits by the coincidence detector are determined. Time delays in the electronic circuits are adjusted to reduce the variance between the determined time differences.

One advantage of at least one embodiment is that it enables changes in signal transit time due to short term drift to be recalibrated frequently.

Advantageously, signal timing can be recalibrated during data acquisition.

Another advantage of at least one embodiment is that it enables timing calibration to be performed with high accuracy.

Still further advantages of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating a preferred embodiment and are not to be construed as limiting the invention.

FIG. 6 is a schematic side view of a fifth embodiment of a portion of a detector head.

Figure 1:
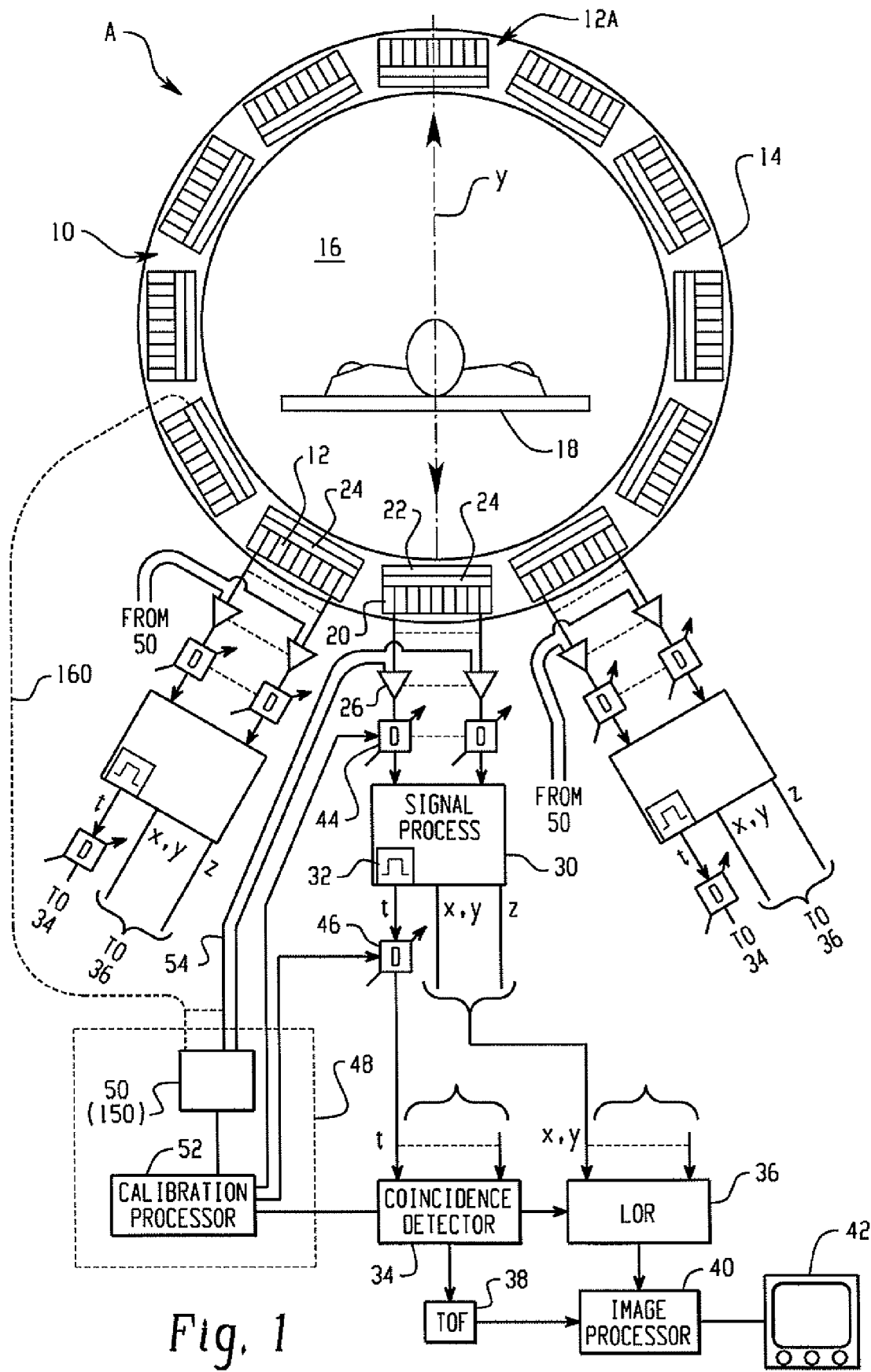
FIG. 1 is a schematic diagram of a gamma camera, energy processing system, and calibration system according to the present invention.

With reference to FIG. 1, a nuclear medicine imaging device A, such as a PET camera, which is suited to coincidence event imaging, includes a detection system 10 comprising a plurality of detector heads 12. In the illustrated embodiment, which shows a dedicated PET imaging device, the detection system includes at least one ring 14 of detector heads 12 positioned around an examination region 16, although it is to be appreciated that the device A may be a multi-head single photon emission computed tomography (SPECT) gamma camera fitted with coincidence circuitry, often referred to as a gamma-PET imaging system. Such systems typically have two or three heads, which are located on a rotatable gantry. A subject support 18 is advanced and retracted to achieve the desired positioning of a subject, such as a patient, within the examination region.

Each detector head 12 detects radiation, such as gamma photons, from a subject in the region 16. In one embodiment, the radiation is the result of the decay of a radiopharmaceutical that has been placed, for example, in the bloodstream of a patient by medical personnel, which decay emits a pair of photons of characteristic energy. It should also be appreciated that the imaging device A may be used in other devices within or outside the medical arts, and the apparatus and method disclosed herein expressly encompasses the use of the gamma camera with these other devices.

Each of the detector heads 12 includes a number of optical sensors 20, such as photomultiplier tubes (PMTs), photodiodes (PDs), or avalanche photodiodes (APDs), which are optically coupled to a continuous or pixelated scintillation crystal 22 by light guides 24, such as glass plates. The glass plates have good optical properties, i.e., contain few flaws and may be contoured to assist in channeling light to the optical sensors. For convenience, particular reference will be made to PMTs, although it is to be appreciated that other optical sensors are also contemplated. A gamma photon interacts with the scintillation crystal 22, generating a pulse of light or scintillation event. Each photomultiplier tube 20 which views the scintillation produces an analogous electrical signal in the form of an event pulse which is proportional to the amount of received light. The pulses are amplified by preamplifiers 26 and processed by a signal processing circuit 30, which includes integrators, threshold circuits, and the like, to determine if a detected event is valid and, if valid, its location (x, y) on the detector head, its energy (z) and timing (i.e., when the radiation was detected). The timing is usually derived from the unshaped signal using a discriminator and time-walk compensation (e.g., CFD).

A coincidence detector 34 receives the trigger signals from all of the detectors and determines whether two events are within a preselected temporal window to be considered simultaneous, i.e., derived from the same annihilation event. If the events are coincident, the coincidence detector 34 enables a line of response (LOR) calculator 36 to determine the line of response (LOR) along which the annihilation event occurred and a time-of-flight (TOF) calculator 38 to determine where along the LOR the annihilation event occurred based on the relative receipt times of the two coincident trigger signals.

The acquired data are stored and processed in image processing and storage 40 which may include a data memory or buffer, a reconstruction processor, for reconstructing an electronic image representation from the data stored in the memory, and an image memory for storing the reconstructed image. Portions of the stored image are retrieved by an image processor which converts the stored image to an appropriate format for display on a display device 42, such as a video, CCD, or: LCD, or active matrix monitor, or other monitor. A color printer or other output device may also be used to present the data in a convenient format.

It will be appreciated that in order to measure location along the LOR accurately, the timing or trigger signals (t) must accurately depict the relative timing between the two scintillation events. Differences in the time required for each photomultiplier tube 20 and its associated signal processing channel to record and to process a scintillation event can be significant (i.e., can produce significant errors) in the time-of-flight calculation. To this end, each channel includes an adjustable delay 44 which is adjusted to equalize the signal processing times. Optionally, each detector head can have an adjustable delay 46 for adjusting for the relative transit times of each trigger signal from its detector head to the coincidence detector. The detector head to coincidence detector balancing can also be achieved by using transmission cables of equal length.

Periodically, such as between each patient examination, or during the patient examination, a timing or trigger signal recalibration circuit 48 adjusts the adjustable delays 44 (or 46) to account for timing variations which arise in the electronic circuitry. In one embodiment, the calibration system 48 includes an electronic source 50, which generates and communicates an electrical calibration pulse directly to the electronics input of the preamplifiers at the output of the detector, bypassing the scintillator 22 and PMTs 20 in the illustrated optical detection embodiment or other non-optical radiation detectors. In another embodiment, the energy source generates light signals which are sent to a light receptive face of the PMTs or other optical detectors.

During calibration, a calibration processor 52 causes the electronic source 50 to apply a synthetic scintillation simulating electrical calibration pulse to each of the preamplifiers 26 using equal length electrical leads 54 and measures the time or relative times for the synthetic signals to reach the coincidence detector. In one embodiment, the synthetic pulses are applied individually and the delay circuits are adjusted to set all channels to a preselected signal transmission time. In another embodiment, two or more synthetic scintillation pulses are applied concurrently and the delay circuits are adjusted such that all the trigger pulses arrive simultaneously. Other measuring and adjustment routines are also contemplated. For example, each of the delay circuits 46 can be adjusted to standardize signal transit times between the heads and then delay circuits 44 can be adjusted to standardize signal times within each head.

The calibration system thus described enables compensation for timing errors which result from changes in the electronics other than the PMT or other detector. The electronics are especially prone to thermal drift. The errors introduced often vary over a relatively short term, such as over several hours or even minutes. By performing the calibration frequently, the errors are compensated for and calculations for TOF-PET analysis retain their accuracy. By using pulses of known characteristics (duration, amplitude, and/or frequency), the calibration can even be performed during a patient scan since the resulting signals can be filtered out from the scan signals.

FIGS. 2-6 illustrate another embodiment of the calibration system for correcting timing errors which includes a light source 150 or other energy source which stimulates the PMTs or other optical detectors to respond. As for the embodiment of FIG. 1, the calibration system is used during calibration of the gamma camera A. The processing steps can be the same as those previously described, except that the energy source is a light source rather than an electrical source and the stimulation is applied further upstream in the data processing channels.

The light source 150 provides a pulse of light. The light can be in the visible region or contain shorter or longer wavelengths, such as ultraviolet (UV) or infrared (IR) wavelengths. In the preferred embodiment, the optical sensors 20 are excited individually or in small defined groups directly with short light pulses from the source 150, without excitation of the scintillation crystal 22. In another embodiment, light from the light source 150 has its wavelength shifted prior to excitation of the sensors 20. In either case, the light pulses can be generated with an intrinsically high time resolution (due to the large number of photons per time interval) and with low jitter with respect to an electrical trigger. This allows the optical sensors to be excited at precisely determined times, and to produce electrical signals with a resolution that is not limited by photon statistics. The remaining timing differences due to the optical sensors and the electronics can then be calibrated.

The light source 150 generates pulses having a wavelength which is detected by the sensors. In one embodiment, the pulses are similar in wavelength to the pulses normally received from the scintillators. As a light source, a laser diode or a light emitting diode can be used. With gain switched laser diodes, light pulses can be generated at about 350-450 nm with a FWHM of <500 ps ($5 \times 10^{-10}$ seconds), a repetition rate of >1 MHz, and a jitter of <10 ps. An exemplary laser diode of this type is a PiLAS ps laser, available from Advanced Photonic Systems. The PiLAS ps laser has a wavelength of 400 nm with a FWHM of <40 ps, a repetition rate of >10 MHz, and a jitter of <4 ps. Other laser sources which produce short light pulses in a suitable wavelength regime (around 400 nm for PMTs) are alternatively used, such as excimer lasers. Light emitting diodes (LEDs) are generally less expensive than laser diodes, and thus it is practicable to use a larger number of these sources in the calibration system. The LEDs may emit in the wavelength range of about 300-600 nm and have a FWHM of <100 ns and a repetition rate of at least 0.1 MHz. LEDs which emit light pulses with a FWHM of <2 ns at 525 nm, with repetition rates up to 10 MHz are available.

The amount of variation in the energy distribution (energy resolution) is typically identified by the full width at half maximum (FWHM) of the distribution. For a normal distribution, FWHM relates to the standard deviation of the distribution and is generally calculated by multiplying the standard deviation by $2 \times (2 \times \ln(2))^{1/2}$ (approximately 2.35).

In the embodiments illustrated in FIGS. 2-6, light is fed from a light source 150 to a plurality of the sensors 20, illustrated as PMTs, via equi-length optical fibers 160 or other suitable light guides, which for convenience, will all be referred to herein as optical fibers. The arrival times of the light pulses at each PMT have a fixed correlation in time. Alternatively, an individual light source is used for each sensor 20. In this case, all sources 150 emit light pulses with a fixed correlation in time. A scintillation crystal 22 is coupled to the PMTs by a light guide 24. Only two PMTs 20 are illustrated in each FIGURE, although it will be appreciated that a single light source 150 may be coupled with a large array of photomultipliers such as are found in an entire detector head or a zone of a detector head or even a plurality of detector heads.

Figure 2:
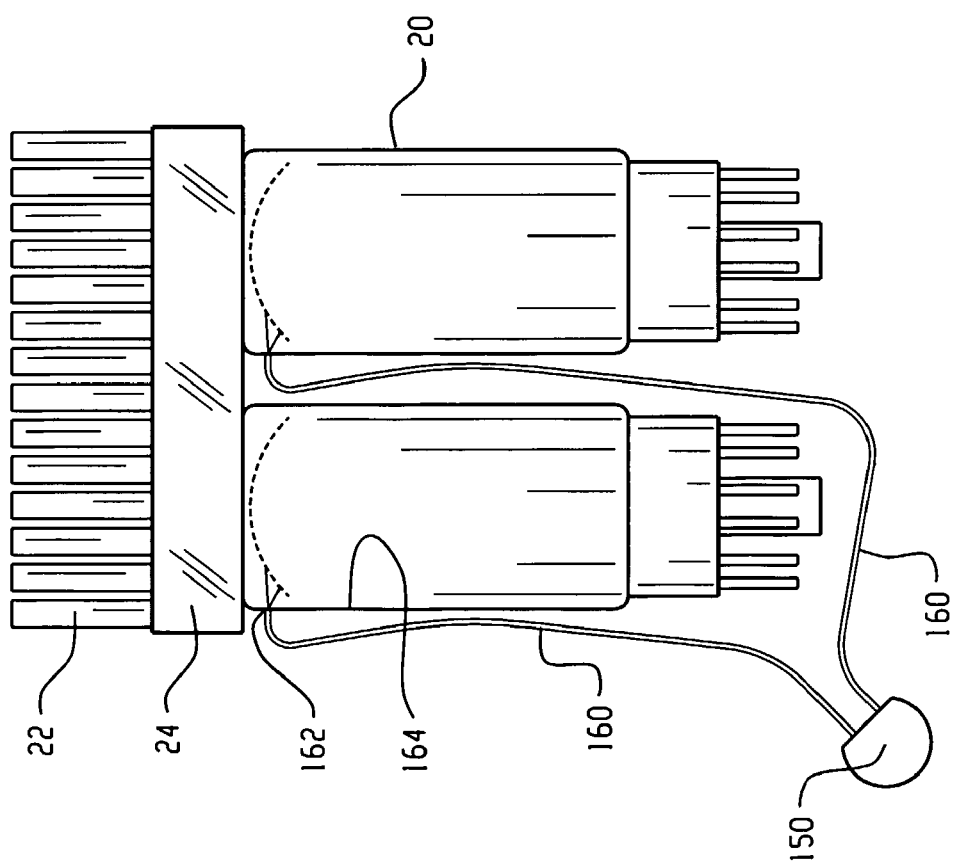
FIG. 2 is a schematic side view of a first embodiment of a portion of a detector head for use with a calibration system according to an embodiment the present invention.

In the embodiment of FIG. 2, to calibrate the camera for timing errors, calibration light pulses are fed individually to each of a plurality of PMTs 20 via respective optical fibers 160 from one source 150, or using individual sources. A fiber end 162 or a light emitter spaced from the end of the optical fiber is coupled to the side wall 164 of each PMT. The signals generated by the PMTs are processed in the manner described above and, the delays 44 set to compensate for timing variations introduced by the PMTs or signal processing components.

Figure 3:
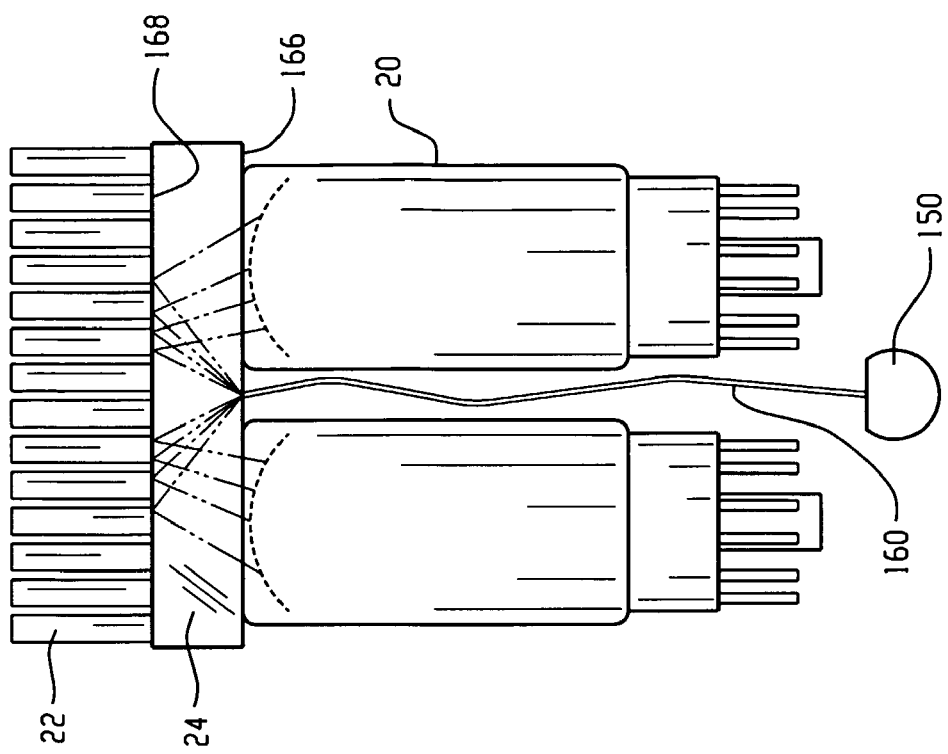
FIG. 3 is a schematic side view of a second embodiment of a portion of a detector head.

In the embodiment of FIG. 3, light pulses are fed to a group of PMTs 20 by a single optical fiber 160. In the illustrated embodiment, the optical fiber is fed into a face 166 of the light guide 24 which is positioned adjacent the PMTs. In the illustrated embodiment, the light from the optical fiber strikes the face at the center of each group of three PMTs (only two are shown). Light from the optical fiber 160 traverses the light guide 24 and is at least partially reflected from an interface 168 between the light guide and the scintillator pixels. The reflected light hits each of the PMTs in the group concurrently.

Figure 4:
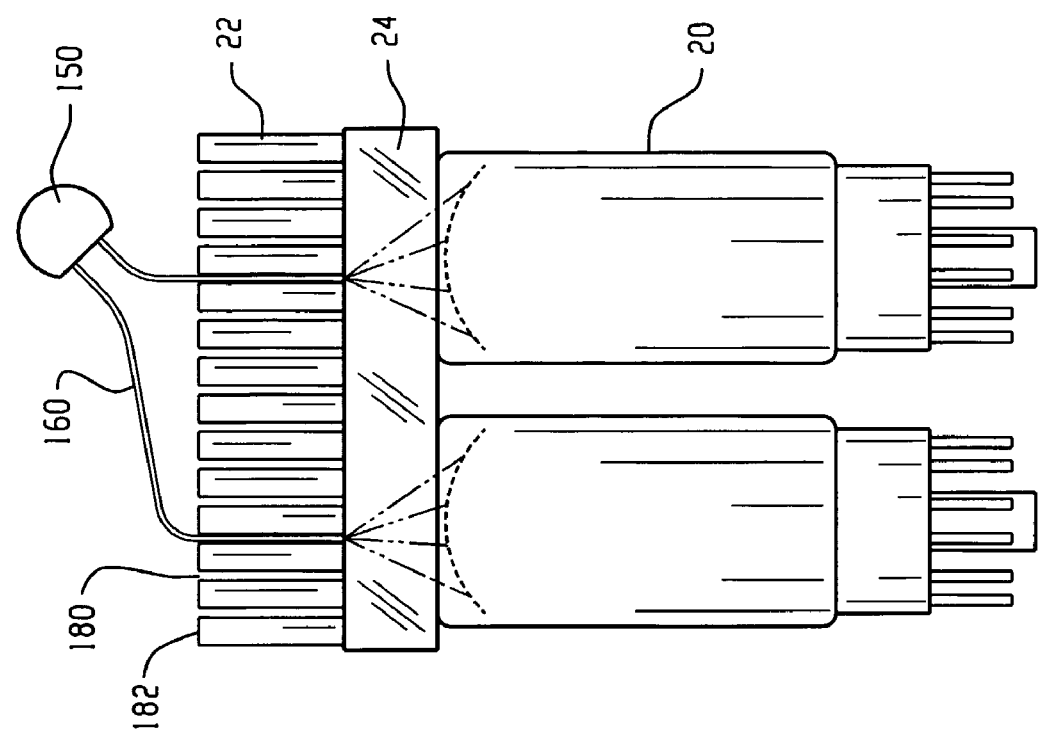
FIG. 4 is a schematic side view of a third embodiment of a portion of a detector head.

FIG. 4 shows another embodiment of the calibration system in which very thin optical fibers 160 extend through the light guide 24, which usually provides an easy access. The optical fibers 160 terminate adjacent a face of each PMT. Alternately, a single optical fiber extends through the light guide across a plurality of PMTs. The optical fiber has a notch in its cladding such that it leaks a point of light at the same preselected position on the face of each of the PMTs. Alternatively, the fiber is coupled to the side wall of the light guide.

In one embodiment, the light guide 24 includes a scatterer, to direct light from the pulse (e.g., a fan beam) to each PMT. In one embodiment, the scatterer includes a plurality of scattering elements 174 (FIG. 4), one associated with each PMT 20. Each scattering element can be at the end of a fiber or defined as an intrusion 174, or a hole in the light guide adjacent each PMT. Alternatively, the scatterer consists of a wavelength shifting material, such as a phosphor or other particulate light scattering material which is distributed in the light guide, particularly in the region of the photomultiplier tubes, although the scattering material may be distributed throughout the light guide 24. Suitable particulate light scattering materials which do not substantially affect the wavelength of the scattered light are formed from micrometer-sized particles of oxide materials, such as rutile ($TiO_2$), hafnia ($HfO_2$), zirconia ($ZrO_2$), magnesium oxide, and the like. Phosphors are particulate materials which convert a portion of the light of one wavelength range to light of a different, typically longer wavelength range, such as yttrium aluminum garnets ("YAG", $Y_3Al_5O_{12}$), activated with Ce or Tb; $Lu_3Al_5O_{12}$ and $Tb_2Al_5O_{12}$, both doped with cerium; $Ca_8Mg(SiO_4)_4Cl_2$, activated with Eu and Mn, and the like, and mixtures thereof. The phosphors act to scatter the light as well as wavelength shifting. In this case, the illumination pulse can be chosen such that the scatterer is excited by the light from the optical fiber, while the PMTs are not excited by light from the optical fiber but are only excited by the wavelength shifted light.

Figure 5:
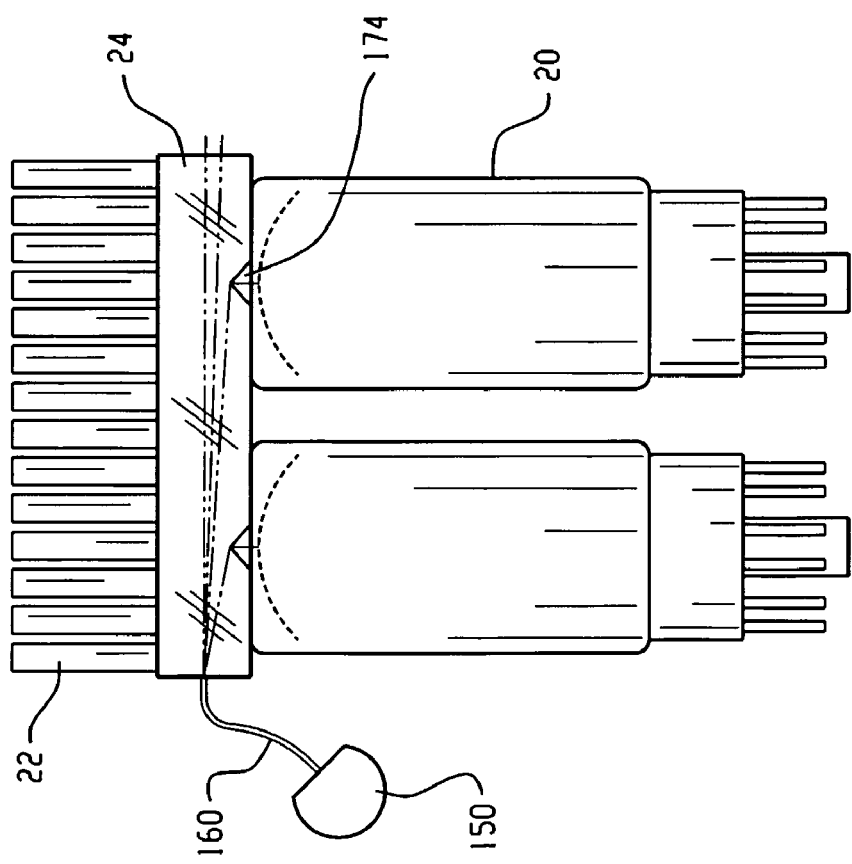
FIG. 5 is a schematic side view of a fourth embodiment of a portion of a detector head.

In the embodiment of FIG. 5, light for calibration is coupled into the light guide 24 from the scintillator 22 side. For example, optical fibers 160 are introduced via gaps 180 between scintillator pixels 182 of a pixilated scintillator, or through the scintillators themselves. As shown in FIG. 6, the fibers 160 are optionally coupled with the top reflective surface of the scintillator 22 (provided it has at least some transmission), so that the light beams travel through the scintillator to the light guide 24 and to the PMTs 20. As with the embodiment of FIG. 6, a scatterer may be used in the light guide, and the photomultipliers may be excited by the wavelength-shifted light, rather than the light emitted by the optical fiber.

As in the embodiment of FIG. 1, the calibration system 48 includes a calibration processor which interrogates inputs to the coincidence detector and calibrates the delays 44 and 46 to correct for timing variations between signals. These variations may be due to the photomultiplier tubes and other components between the PMTs and the coincidence detector including the electronics.

It will be appreciated that the gamma camera A optionally includes both optical and electronic calibration.

Periodically, the imaging device may be calibrated with a radiation source. The calibration allows timing variations due to differences in the scintillator crystals 24 to be determined and corrections made.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiment, the invention is now claimed to be:

1. A PET nuclear imaging device comprising:
   an array of radiation detectors which generate output signals in response to receiving radiation;
   an array of electronic circuits processing the output signals from corresponding detectors of the array of detectors;
   a coincidence detector;
   image processing circuitry; and
   a calibration system including:
      an energy source which generates electrical pulses which are communicated to each of the electronic circuits, each electrical pulse causing the electronic circuit which receives the electrical pulse to generate the trigger pulse in an absence of a radiation detector receiving radiation,
      a calibration processor which determines differences in time of receipt of the trigger pulse from each of the electronic circuits by the coincidence detector, the calibration processor adjusting programmable delays in each of the electronic circuits to reduce the determined time differences.

2. A PET camera including the calibration circuit of claim 1.

3. A time-of-flight PET nuclear imaging system including:
   optical sensors;
   electronic circuits for processing output signals from the optical sensors;
   a coincidence detector;
   image processing circuitry; and
   a calibration system comprising:
   a light source which generates calibration light pulses;
   a plurality of optical fibers optically coupled to the light source, the optical fibers delivering the calibration light pulses the optical causing the electronic circuits to generate trigger pulses indicative of times the calibration light pulses are received,
   a calibration processor which determines differences in time of receipt of the trigger pulse from each of the electronic circuits by the coincidence detector, the calibration processor adjusting programmable delays in each of the electronic circuits to reduce the determined time differences.

4. The system according to claim 3, wherein the calibration pulses are of known or fixed frequency.

5. The system according to claim 3, wherein each calibration pulse has a FWHM of <10 ns and a frequency of >0.1 MHz.

6. The system according to claim 3, wherein the light source has a wave length of 300-600 nm.

7. The system according to claim 3, wherein the light source includes a light emitting diode or laser diode.

8. The system according to claim 3, wherein the optical fibers are coupled directly with light input faces of the optical sensors.

9. The system according to claim 3, wherein a single optical fiber is coupled with the plurality of optical sensors.

10. The system according to claim 9, wherein the single optic fiber includes at least one of an intrusion and a light scattering particulate material.

11. A PET camera including the calibration system according to claim 3.

12. The system according to claim 3, wherein the light source includes a laser.

13. A method for calibrating a nuclear imaging system for calibration of a PET nuclear imaging device which includes an array of optical sensors, electronic circuits for processing output signals from each optical sensor of the array of optical sensors, a coincidence detector, and imaging processing circuitry, the method comprising:

activating a light source to generate light calibration pulses; fiber optically transmitting the light calibration pulses to a common location on a light receiving face of each optical sensor of the array of optical sensors to cause the electronic circuits to generate trigger pulses, the trigger pulses traveling to the coincidence detector;

determining differences in time between generation of the light calibration pulses and receipt of the trigger pulses from each of the electronic circuits with the coincidence detector;

adjusting time delays in the electronic circuits to reduce the variance between the determined time differences.

14. The method according to claim 13, wherein the adjusting step includes adjusting the time delays to set the time between the calibration pulse and receipt of the trigger pulse to a preselected time.

15. An electronic processor programmed to perform the method according to claim 13.

16. The method according to claim 13, wherein the light source includes a laser.

17. A method for calibrating a nuclear imaging system for calibration of a PET nuclear imaging device which includes radiation detectors, electronic circuits for processing output signals from the detectors, a coincidence detector, and image processing circuitry, the method comprising:

activating an energy source to generate calibration pulses, the calibration pulses being electrical pulses;

feeding the calibration pulses into inputs to the electronic circuits at outputs from the radiation detectors to cause the electronic circuits to generate trigger pulses, the trigger pulses traveling to the coincidence detector, wherein the electrical pulses are communicated directly to the electronic circuits bypassing the radiation detectors;

determining differences in time between generation of the calibration pulse and receipt of the trigger pulses from each of the electronic circuits by the coincidence detector;

adjusting time delays in the electronic circuits to reduce the variance between the determined time differences, wherein the energy source generates electrical pulses which are communicated directly to the electronic circuits bypassing the radiation detectors.

* * * * *